US007396528B2

(12) United States Patent
Williams et al.

(10) Patent No.: US 7,396,528 B2
(45) Date of Patent: Jul. 8, 2008

(54) CORNEAL CELLS EXPRESSING ACTIVE AGENTS AND METHODS OF USE THEREOF

(76) Inventors: Keryn Anne Williams, 17 E. Parade, Kingswood, S. Australia 5062 (AU); Douglas John Coster, 3 Newcastle St, Heathpool, S. Australia, 5068 (AU); Sonja Klebe, 4 Yatina Road, Aldgate, S. Australia, 5154 (AU)

( * ) Notice: Subject to any disclaimer, the term of this patent is extended or adjusted under 35 U.S.C. 154(b) by 0 days.

(21) Appl. No.: 11/343,971

(22) Filed: Jan. 30, 2006

(65) Prior Publication Data

US 2006/0257382 A1    Nov. 16, 2006

Related U.S. Application Data

(60) Division of application No. 10/293,385, filed on Nov. 12, 2002, now abandoned, which is a continuation of application No. 09/834,050, filed on Apr. 11, 2001, now abandoned.

(30) Foreign Application Priority Data

Oct. 11, 2000    (AU) .................................. PR 0695

(51) Int. Cl.
*A61K 48/00*    (2006.01)
(52) U.S. Cl. .................. 424/93.21; 424/93.1; 424/93.2; 514/44; 435/320.1
(58) Field of Classification Search .................. None
See application file for complete search history.

(56) References Cited

U.S. PATENT DOCUMENTS 5,770,580 A    6/1998    Ledley et al.
6,338,851 B1    1/2002    Gorczynski

FOREIGN PATENT DOCUMENTS

WO    WO 96/13276    5/1996

OTHER PUBLICATIONS

Peterson, Statement of Amy Patterson M.D., Feb. 2000.*
Orkin et al. NIH Report, Dec. 1995.*
Arancibia-Carcamo, C. V., et al., "Lipoadenofection-Mediated Gene Delivery to the Corneal Endothelium," *Transplantation*, 65(1):62-67 (1998).
Bloom, David C., et al., "Long-term expression of a reporter gene from latent herpes simplex virus in the rat hippocampus," *Molecular Brain Research* 31:48-60 (1995).
Boehler, A., et al., "Adenovirus-Mediated Interleukin-10 Gene Transfer Inhibits Post-Transplant Fibrous Airway Obliteration in an Animal Model of Bronchiolitis Obliterans," *Human Gene Therapy*, 9:541-551 (1998).
Borras, T., et al., "Ocular Adenovirus Gene Transfer Varies in Efficiency and Inflammatory Response," *Investigative Ophthalmology & Visual Science*, 37(7):1282-1293 (1996).
Brauner,MD., R., et al., "Intracoronary Adenovirus-Mediated Transfer of Immunosuppressive Cytokine Genes Prolongs Allograft Survival," *J. Thoracic and Cardio. Surg.*, 114(6):923-933 (1997).
Budenz, Donald L., et al., "In Vivo Gene Transfer Into Murine Corneal Endothelial and Trabecular Meshwork Cells," *Investigative Ophthalmology & Visual Science*, 36(11):2211-2215 (1995).
Byrnes, A.P., et al., "Adenovirus Gene Transfer Causes Inflammation in the Brain," *Neuroscience* 66(4):1015-1024 (1995).
DeBruyne, LA., et al., "Lipid-mediated gene transfer of viral IL-10 prolongs vascularized cardiac allograft survival by inhibiting donor-specific cellular and humoral immune responses," *Gene Therapy*, 5:1079-1087 (1998).
Fehervari, Z., et al., "Gene Transfer to Ex Vivo Stored Corneas," *Cornea*, 16(4):459-464 (1997).
Gogolin-Ewens, K.J., et al., "Sheep lymphocyte antigens (OLA)," *Immunology*, 56:717-723 (1985).
Goldman, Mitchell J., et al., "Transfer of the CFTR Gene to the Lung of Nonhuman Primates with E1-Deleted, E2a-Defective Recombinant Adenoviruses: A Preclinical Toxicology Study," *Human Gene Therapy*, 6:839-851 (1995).
Graham, F.L., et al., "Characteristics of a Human Cell Line Transformed by DNA from Human Adenovirus Type 5," *J. Gen. Virol.*, 36:59-72 (1977).
Graham, Frank L. and Prevec, Ludvik, "Manipulation of Adenovirus Vectors," *Methods in Molecular Biol.*, 7:109-128 (1991).
Griffith, Thomas S. and Ferguson, Thomas A., "The role of FasL-induced apoptosis in immune privilege," *Immunology Today*, 18(5): (1997).
Grooby, W.L., et al., "Use of an Anti-LFA-1 Antibody in Renal Allograft Rejection in Sheep," *Transplantation Proceedings*, 24(5):2304 (1992).
Hoffman, Lisa M., et al., "Cell-Mediated Immune Response and Stability of Intraocular Transgene Expression After Adenovirus-Mediated Delivery," *Investigative Ophthalmology & Visual Science*, 38(11):2224-2233 (1997).
Holland, Edward J., et al., "Clinical and Immunohistologic Studies of Corneal Rejection in the Rat Penetrating Keratoplasty Model," *Cornea* 10(5):374-380 (1991).
Hudde, T., et al., "Activated polyamidoamine dendrimers, a non-viral vector for gene transfer to the corneal endothelium," *Gene Therapy*, 6:939-943 (1999).
Kanegae, Y., et al., "A Simple and Efficient Method for Purification of Infectious Recombinant Adenovirus," *Jnp. J. Med. Sci. Biol.*, 47:157-166 (1994).
Larkin, D.F.P., et al., "Adenovirus-Mediated Gene Delivery To The Corneal Endothelium," *Transplantation* 61(3):363-370 (1996).

(Continued)

*Primary Examiner*—Q. Janice Li
(74) *Attorney, Agent, or Firm*—Hamilton, Brook, Smith & Reynolds, P.C.

(57) ABSTRACT

The invention relates to methods of modifying cells of corneal tissue to express an active agent, to modified corneal tissue, to vectors utilised in such methods and to methods of xeno- and allo-transplantation utilising the modified corneal tissue. The method of modifying cells of corneal tissue to express an active agent involves exposing harvested corneal tissue to an effective concentration for transfection of an expression vector which comprises a nucleotide sequence encoding for the active agent for a period sufficient to allow infection, such that cells of the corneal tissue will express the active agent.

21 Claims, 4 Drawing Sheets

OTHER PUBLICATIONS

Mackay, C.R., et al., "Characterization of two sheep lymphocyte differentiation antigens SBU-T1 and SBU-T6," *Immunology* 55:729-737 (1985).

Mackay, Charles Reay, et al., "Three Distinct Subpopulations of Sheep T Lymphocytes," *Eur. J. Immunol.* 16:19-25 (1986).

Maddox, J.F., et al., "Surface Antigens, SBU-14 and SBU-T8, of Sheep T Lymphocyte Subsets Defined by Monoclonal Antibodies," *Immunology* 55:739-748 (1985).

Maddox, J.F., et al., "The Sheep Analogue of Leucocyte Common Antigen (LCA)," *Immunology* 55:347-353 (1985).

Malefyt, R. deWaal, et al., "Interleukin-10," *Curr. Opinion in Immunology* 4:314-320 (1992).

Martin H.M., et al., "Cloning and characterisation of an ovine interleukin-10-encoding cDNA," *Gene* 159:187-191 (1995).

Moore, KW., et al., "Interleukin-10," Annual Reviews *Immunol.* 11:165-90 (1993).

Oral, HB., et al., "Ex vivo adenovirus-mediated gene transfer and immunomodulatory protein production in human cornea," *Gene Therapy* 4:639-647 (1997).

Palmer, Theo D., et al., "Genetically modified skin fibroblasts persist long after transplantation but gradually inactivate introduced genes," *Proc. Natl. Acad. Sci. USA* 88:1330-1334 (1991).

Pepose, Jay S., et al., "Detection of HLA Class I and II Antigens in Rejected Human Corneal Allografts," *Ophthalmology* 92(11):1480-1484 (1985).

Philipson, Lennart, et al., "Virus-Receptor Interaction in an Adenovirus System," *J. Virology* 2:1064-1075 (1968).

Pleyer, U., et al., "Liposome-mediated gene transfer into corneal endothelial cells," *Invest. Ophthalmol. Vis. Sci.*, 38: S402 (1997).

Puri, N.K., et al., "Sheep lymphocyte antigens (OLA)," *Immunology* 56:725-733 (1985).

Qian, Shiguang, et al., "Systemic Administration of Cellular Interleukin-10 Can Exacerbate Cardiac Allograft Rejection in Mice," *Transplantation* 62(12):1709-1714 (1996).

Qin, L., et al., "Retrovirus-Mediated Transfer of Viral IL-10 Gene Prolongs Murine Cardiac Allograft Survival," *J. Immunology*, pp. 2316-2323 (1996).

Qin, Lihui, et al., "Adenovirus-Mediated Gene Transfer of Viral Interleukin-10 Inhibits the Immune Response to Both Alloantigen and Adenoviral Antigen," *Human Gene Therapy* 8:1365-1374 (1997).

Raisanen-Sokolowki, Anne, et al., Heart Transplants in Interferon-γ, Interleukin 4, and Interleukin 10 Knockout Mice, *J. Clin. Invest.* 100(10):2449-2456 (1997).

Raisanen-Sokolowki, Anne, et al., "Leukocyte-Suppressing Influences of Interleukin (IL)-10 in Cardiac Allografts," *Am. J. Pathology* 153(5):1491-1500 (1998).

Sano, Yoichiro, et al., "Cytokine Expression during Orthotopic Corneal Allograft Rejection in Mice," *IVOS* 39(10):1953-1957 (1998).

Seth, Prem, et al., "Evidence that the Penton Base of Adenovirus Is Involved in Potentiation of Toxicity of *Pseudomonas* Exotoxin Conjugated to Epidermal Growth Factor," *Molecular and Cellular Biology* 4(8):1528-1533 (1984).

Sherrard, Emil S., "The Corneal Endothelium in vivo: its Response to Mild Trauma," *Exp. Eye Res.* 22:347-357 (1976).

Shinozaki, K., et al. "Allograft transduction of IL-10 prolongs survival following orthotopic liver transplantation," *Gene Therapy* 6:816-822 (1999).

Simonsen, A. Hjorth, "Thymidine Incorporation by Human Corneal Endothelium During Organ Culture," *ACTA Ophthalmologica* 59:110-118 (1981).

Torres, Paulo F., et al. "Interleukin 10 Treatment Does Not Prolong Experimental Corneal Allograft Survival," *Ophthalmic Res.* 31:297-303 (1999).

Treffers, MD., W. Frits, "Human Corneal Endothelial Wound Repair," *Ophthalmology* 89:605-613 (1982).

Tuft, Stephen J., "Endothelial Repair in the Rat Cornea," *Invest. Ophthalmol Vis. Sci.* 27:1199-1204 (1986).

Tuft, S.J. and Coster, D.J., "The Corneal Endothelium," *Eye* 4:389-424 (1990).

Van Horn, Diane L., et al., "Regenerative capacity of the corneal endothelium in rabbit and cat," *Invest. Ophthalmol. Visual Sci.*, 16(7):597-613 (1977).

Whitcup, Scott M., et al., "Expression of Cell Adhesion Molecules in Corneal Graft Failure," *Cornea* 12(6):475-480 (1993).

Williams, KA., et al., "A new model of orthotopic penetrating corneal transplantation in the sheep: Graft survival, phenotypes of graft-infiltrating cells and local cytokine production," *Australian and New Zealand J. Ophthal.* 27:127-135 (1999).

Williams, Keryn Anne and Coster, Douglas John, "Clinical and Experimental Aspects of Corneal Transplantation," *Transplantation Reviews*, 7(1):44-64 (1993).

Williams Keryn A., et al., "How Successful is Corneal Transplantation? A Report from the Australian Corneal Graft Register," *Eye* 9:219-227 (1995).

Zou, Xiao Ming, et al., "Downregulation of Cytokine-induced Neutrophil Chemoattractant and Prolongation of Rat Liver Allograft Survival by Interleukin-10," *Jpn J Surg.* 28:184-191 (1998).

Noisakran, Sansanee, et al., "Ectopic Expression of DNA Encoding IFN-α1 in the Cornea Protects Mice from Herpes Simplex Virus Type 1-induced Encephalitis," *J. of Immunology* 162:4184-4190 (1999).

Orkin, M.D., Stuart H. and Motulsky, M.D., Arno G., "Report and Recommendations of the Panel to Assess the NIH Investment in Research on Gene Therapy," Dec. 7, 1995.

Patterson, M.D., Amy, Office of Biotechnology Activities, Before the Subcommittee on Public Health, Feb. 2, 2000.

Qin, Lihui, et al., "Multiple Vectors Effectively Achieve Gene Transfer in a Murine Cardiac Transplantation Model," *Transplantation* 59(6):809-816 (1995).

Tsubota, Kazuo, et al., "Adenovirus-Mediated Gene Transfer to the Ocular Surface Epithelium," *Exp. Eye Res.* 67:531-538 (1998).

Klebe, S., et al., "Expression of Interleukin-10 In Donor Corneal Endothelium Prolongs Graft Survival in Sheep," The Transplant Society of Australia and New Zealand 18th Scientific Meeting, Abstract No. 37.

Daheshia, M., et al., "Suppression of Ongoing Ocular Inflammatory Disease by Topical Administration of Plasmid DNA Encoding IL-10[1]," *J. Immunol.*, 159:1945-1952 (1997).

König Merediz, S.A., et al., "Ballistic Transfer of Minimalistic Immunologically Defined Expression Constructs for IL4 and CTLA4 Into the Corneal Epithelium in Mice After Orthotopic Corneal Allograft Transplantation," *Graefes Arch. Clin. Exp. Opthalmol.* 238:701-707 (2000).

Pleyer, U., et al., "Survival of Corneal Allografts Following Adenovirus-Mediated Gene Transfer of Interleukin-4," *Graefes Arch. Clin. Exp. Opthalmol* 238:531-536 (2000).

Ritter, et al., "Adenovirus-Mediated Gene Transfer of Interleukin-4 to Corneal Endothelial Cells and Organ Cultured Corneas Leads to High IL-4 Expression," *Exp. Eye Res.*, 69: 563-568 (1999).

Oral, et al., "Ex vivo Adenovirus-Mediated Gene Transfer and Immunodulatory Protein Production in Human Cornea," *Gene Therapy*, 4: 639-647 (1997).

\* cited by examiner

A

B

CORNEAL CELLS EXPRESSING ACTIVE AGENTS AND METHODS OF USE THEREOF

RELATED APPLICATIONS

This application is a divisional of U.S. application Ser. No. 10/293,385, filed Nov. 12, 2002 now abandoned, which is a continuation of U.S. application Ser. No. 09/834,050 filed Apr. 11, 2001 now abandoned which claims the benefit of Australian Patent Application No. PR0695/00 filed on Oct. 11, 2000. The teachings of both referenced applications are incorporated herein by reference in their entireties.

BACKGROUND OF THE INVENTION

There are numerous diseases and disorders that can effect corneal tissue and which can, as a result, adversely effect or eliminate vision. For example, allergies, conjunctivitis, corneal infections, Fuchs' dystrophy (deterioration of corneal endothelial cells), varicella-zoster virus, iridocomeal endothelial syndrome, keratoconus, ocular herpes and a number of other conditions, as well as congenital corneal abnormalities can be responsible for corneal damage or irregularity that may affect vision. In an endeavour to restore sight or improve vision in people suffering from corneal abnormalities it has become particularly common to perform corneal transplant operations where the abnormal corneal tissue is removed and replaced using fine sutures with normal corneal tissue obtained from a donor. Although corneal transplant operations enjoy a high rate of success there are nonetheless some problems which can occur, such as rejection of the replacement cornea and ocular fibrosis or scarring. Even in the case of a successful corneal transplantation it is necessary for subsequent administration of immunomodulatory agents. Non-compliance by the patient with prescribed dosing regime of immunomodulating agents may give rise to tissue rejection. There is, accordingly, a need for improved means of prolonging corneal graft survival and preventing tissue rejection as well as for the provision of approaches for therapy of ocular infection, wounds and fibrosis and for therapy of other ocular disorders, for example.

The cornea is a highly organised group of cells and proteins which unlike most tissue is clear, and does not contain blood vessels to nourish or protect against infection. The cornea receives nutritional supply from tears and the aqueous humor found in the anterior chamber located behind it. The cornea is composed of five basic layers, namely the protective external epithelium, Bowman's layer which is located below the epithelial basement membrane and is composed of collagen fibers, the stroma which consists primarily of water and collagen and is located beneath Bowman's layer; and Descemet's membrane located beneath the stroma, which is composed of collagen fibers produced by the endothelial cells located in the lower endothelium. The endothelial cells are essential in maintaining clarity of the cornea by removing excess fluid from the stroma.

Irreversible immunological rejection is the major cause of human corneal graft failure (1), despite the immunologically privileged nature of the eye (2). The histological correlates of rejection include local upregulation of major histocompatability complex and adhesion molecules, an influx of mononuclear cells into the cornea and anterior chamber, and local production of some inflammatory cytokines (3-7). The major target of corneal graft rejection is the corneal endothelium. Human (but not rodent) corneal endothelium is essentially amitotic (8), so that damage to the monolayer during graft rejection cannot be repaired.

Gene therapy has the potential to influence an allograft response through local expression of a modulatory gene product within transplanted donor tissue. The present inventors consider that the cornea may be uniquely amenable to such an approach because of its small size, which may allow modification of the whole tissue, and because of the ease with which a donor cornea may be manipulated in vitro and stored for a considerable period (for example, up to 28 days) prior to transplantation. The anatomical location and clarity of the cornea allow in vivo assessment of the entire graft in the post-operative period and loss of function is easy to detect. Furthermore, the cornea and anterior chamber are at least partially immunologically privileged sites (2), which may allow the use of otherwise immunogenic or pro-inflammatory vectors.

SUMMARY OF THE INVENTION

According to one embodiment of the present invention there is provided a method of modifying cells of corneal tissue to express an active agent comprising exposing harvested corneal tissue to an effective concentration for infection of an expression vector which comprises a nucleotide sequence encoding for the active agent for a period sufficient to allow transfection, e.g., infection, such that cells of said corneal tissue will express the active agent.

According to another embodiment of the present invention there is provided a corneal tissue comprising cells modified to express an active agent which is not expressed by normal corneal tissue or which following modification is expressed at elevated levels relative to normal corneal tissue.

In embodiments, the nucleotide sequence utilized in the methods of the invention can be any type of nucleic acid, e.g., DNA or RNA. The nucleic acid can be a full-length gene or an active portion of the gene.

In another embodiment of the invention there is provided a corneal tissue comprising cells modified to express an active agent, wherein modification is by exposing harvested corneal tissue to an effective concentration for transfection, e.g., infection of an expression vector which comprises a nucleotide sequence encoding for the active agent, for a period sufficient to allow infection.

In a further embodiment of the invention there is provided a method of improving corneal graft healing and/or prolonging graft survival comprising exposing harvested corneal tissue to an effective concentration for infection of an expression vector which comprises a nucleotide sequence encoding for an active agent for a period sufficient to allow transfection, e.g., infection, such that cells of said corneal tissue will express the active agent, and then transplanting the corneal tissue to an eye of a recipient.

In a still further embodiment of the invention there is provided an expression vector for use in modifying corneal tissue to express an active agent not expressed by normal corneal tissue or which following modification is expressed at elevated levels relative to normal corneal tissue; the vector comprising a nucleotide sequence encoding for the active agent.

Preferably the active agent is a peptide hormone, a cytokine or an analogue thereof. In a preferred embodiment of the invention the cytokine is an interleukin, an interferon or a growth factor, or an analogue thereof. In preferred embodiments of the invention the cytokine is selected from the interleukins including IL-10, IL-4, the P-40 component of IL-12 or from Bcl2, interferon Gamma, interferon Alpha and TGF Beta.

In preferred embodiments of the invention the corneal tissue is harvested from a mammal, particularly preferably from a human. Preferably the recipient of transplanted corneal tissue is a mammal, particularly preferably a human. In a particularly preferred embodiment of the invention corneal tissue is harvested from a human and transplanted to another human recipient.

In a preferred embodiment of the invention the corneal tissue cells modified are epithelial cells, stroma cells and/or endothelial cells. Particularly preferably, the modified cells are endothelial cells. In a preferred embodiment of the invention 5%, preferably at least 10%, more preferably at least 20%, particularly preferably at least 30% or at least 50% and most particularly preferably at least 70% of corneal endothelial cells in a sample of corneal endothelial cells are modified by methods according to the invention.

In preferred embodiments of the invention the expression vector is a viral, bacterial or plasmid vector. In particularly preferred embodiments of the invention the expression vector is an adeno-associated viral vector or an adenoviral vector.

Preferably the effective concentration for transfection, e.g., infection is between about $1 \times 10^5$ to $1 \times 10^{10}$ particle forming units (pfu) per cornea. Particularly preferably the effective concentration for infection is between about $5 \times 10^5$ to $5 \times 10^8$ pfu/cornea, more particularly preferably between about $2 \times 10^6$ and about $9 \times 10^7$ pfu/cornea.

In a preferred embodiment of the invention the period sufficient to allow transfection, e.g., infection is between about 1 minute and about 48 hours, particularly preferably between about 10 minutes and 24 hours, more particularly preferably between about 30 minutes and 6 hours and most particularly preferably between about 1 hour and about 3 hours.

In another preferred embodiment of the invention the expression vector comprises DNA sequences encoding for two or more active agents.

BRIEF DESCRIPTION OF THE DRAWINGS

The foregoing and other objects, features and advantages of the invention will be apparent from the following more particular description of preferred embodiments of the invention, as illustrated in the accompanying drawings.

FIG. 1(A) shows uptake in endothelial cells (arrowed) at margins of deliberate injury, magnification ×32; FIG. 1(B) shows high power view showing mitotic figure (arrowed); magnification ×128.

FIG. 2(A) shows concentrations of Ad-lacZ from $6.6 \times 10^2$ to $6.6 \times 10^8$ pfu per cornea were used to transfect ovine corneas in vitro under otherwise identical conditions. Corneas were harvested 48 hours later. Each bar represents the mean percentage positive cells ±SD of counts from 3 to 6 corneas. FIG. 2(B) shows ovine corneas were incubated with Ad-lacZ at $6.6 \times 10^6$ and $6.6 \times 10^7$ pfu per cornea for 0.5-2.0 h. Corneas were harvested 48 hours later. Each bar represents the mean percentage of positive cells ±SD from 3 organ-cultured corneas. FIG. 2(C) shows duration of expression of β-galactosidase in organ-cultured ovine corneas after transfection with $6.6 \times 10^6$ Ad-lacz pfu per cornea for 2 hours. Corneas were harvested at the indicated time-points. Each point represents the mean percentage positive cells ±SD of 3-14 corneas.

FIG. 4(A) shows rejecting unmodified allograft, day 29 post-graft; FIG. 4(B) shows surviving IL-10-modified allograft, day 190 post-graft.

DETAILED DESCRIPTION OF THE INVENTION

Figure 1:
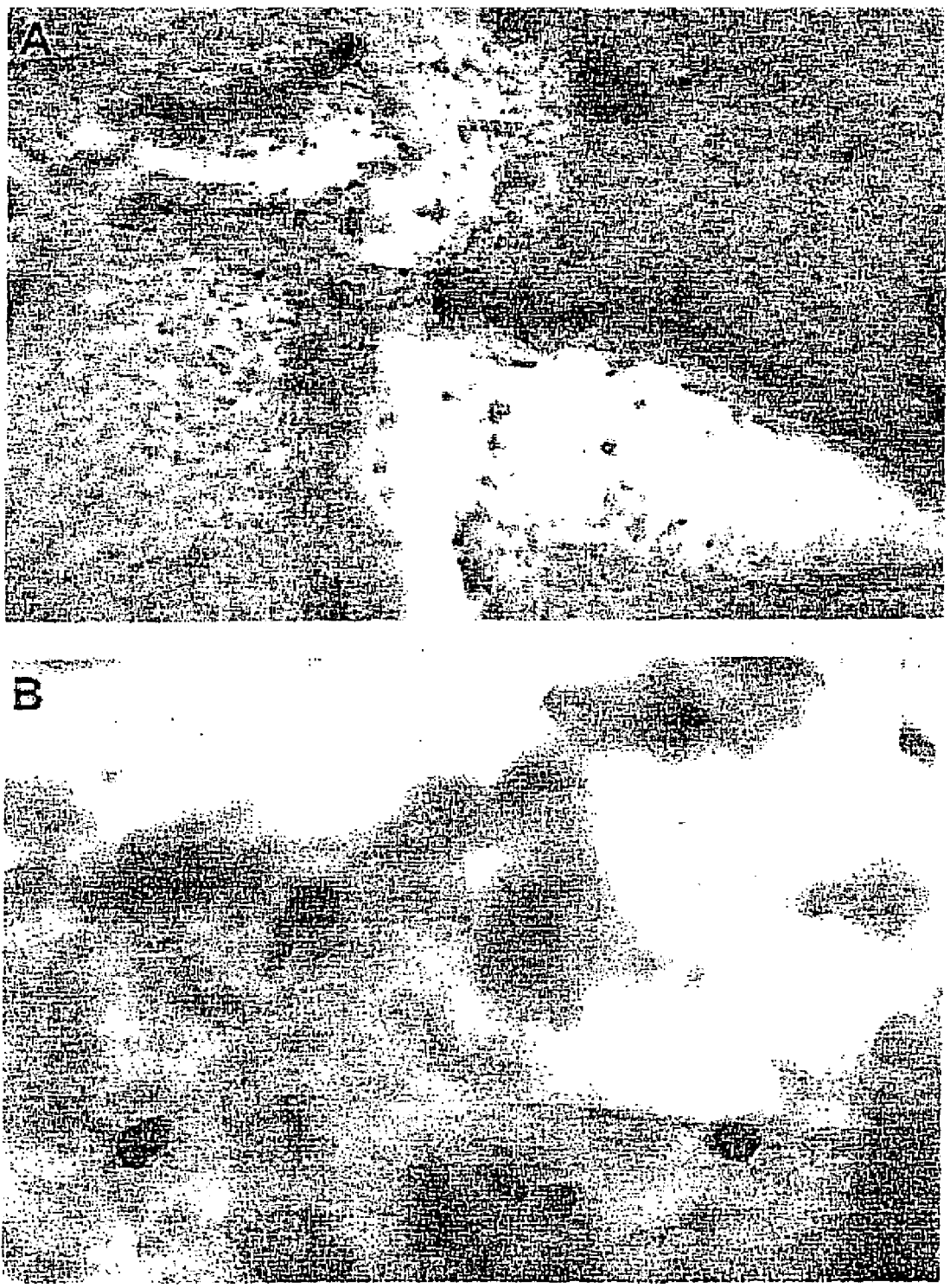
FIG. 1. Autoradiographs showing uptake of $^3$H thymidine in organ-cultured ovine corneal endothelium, 3 days after deliberate injury.

As indicated above the present inventors have devised an approach for treating ocular disorders and demonstrated its efficacy in a sheep model. In the specifically exemplified embodiments of the present invention harvested corneal tissue has been modified to express immunomodulatory agents having the effect of prolonging corneal graft survival once implanted into a recipient, relative to the expected survival time in the case where no immunomodulatory agent is administered. However, the present invention has considerably broader application than simply its use in association with corneal allo- or xeno-transplantation techniques. Methods according to the present invention may be adopted for treatment of other ocular disorders such as, for example, the treatment of ocular wounds, infections or fibrosis or of other ocular diseases such as glaucoma, keratoconus, corneal dystrophies, corneal infections, tumors of the eye, proliferative lesions, pterygium and inflammatory disorders of the eye including Stevens-Johnson syndrome and mucous panphigoid. Reference to the term "treatment" is intended to include both therapeutic and prophylactic treatments.

One aspect of the invention relates to methods of modifying cells of corneal tissue to express an active agent. As these active agents are to be expressed in the corneal tissue cells as a result of gene transfer, the active agents will of course constitute peptides, polypeptides or proteins, the expression of which can be encoded for by nucleotide, particularly sequences. Collectively, such active agents, regardless of the peptide sequence, may be referred to herein as "peptides". The active agents according to the invention may for example constitute naturally occurring or synthetic peptide hormones, cytokines or analogues thereof. By use of the term "analogue" it is intended to embrace modified forms of naturally occurring or synthetic peptide hormones or cytokines having physiological activity which may for example be modified relative to the molecule upon which they are based by the addition, deletion or substitution of single or multiple amino acids.

Examples of active agents that may be expressed by the methods and vectors according to the present invention include peptide hormones and cytokines and analogues thereof which may for example have immunomodulatory, anti infective, tissue regeneration, wound healing or fibrosis reduction activity. Cytokines that may be adopted in the present invention include those selected from the interleukins, the interferons and the growth factors as well as analogues thereof. Specific examples of cytokines that may be adopted include IL-10, IL-4, the P-40 component of IL-12, Bcl2, interferon gamma, interferon alpha and TGF beta. It is to be understood however that these specific cytokines are mentioned as active agents by way of example only, and that other peptide agents with useful activity may equally be adopted.

The corneal tissue to be modified according to the present invention will generally have been harvested from a donor, usually a donor mammal. Preferably the donor will be selected from the same species as the corneal transplant recipient and generally from a donor having matching tissue and/or blood types as the intended recipient, as well understood in the art. There may, however, be circumstances, such as if there is insufficient donor organ supply from members of the same species (allo-transplantation), where corneal tissue is harvested from a donor member of another species (xeno-transplantation). In the case of xeno-transplantation the tissue donor may be an animal that has been genetically modified to remove or reduce the impact of species specific immunogenic differences. It may also be possible in future for corneal tissue to be produced by organ culture techniques which can then similarly be harvested for modification by methods according to the present invention.

Mammals from which corneal tissue may be harvested and/or to which corneal tissue may be transplanted include, but are not limited to, humans, farm animals including cattle, sheep, goats, pigs, horses, etc.; captive wild animals including lions, tigers, deer, chimpanzees, apes, gorillas, baboons, etc.; domestic animals such as cats and dogs, etc, or laboratory animals such as rabbits, mice, guinea pigs, rats and the like. Preferably the corneal tissue is harvested from a human donor for transplant to a human recipient. In the case of human corneal tissue donors, the donor will generally be a person registered as an organ donor who has met an untimely death, and whose corneal tissue is in good condition. In the case of animal donors, the animal may be sacrificed in order to harvest the corneal tissue or may in fact be sacrificed for other purposes such that the corneal tissue becomes available.

The corneal tissue will preferably be obtained from the donor within a relatively short period post mortem, preferably within three to four hours and particularly preferably within the first hour. The conditions under which the corneal tissue should be removed from the donor and maintained prior to modification are a matter of routine and are well understood by persons skilled in the art. Naturally, the use of a suitable tissue culture media is required to maintain the tissue in a healthy state prior to modification and transplantation. Preferably modification of the corneal tissue will be conducted within a matter of a few hours from harvesting of the tissue, although it is possible to maintain corneal tissue under tissue culture conditions for up to about 28 days.

The expression vector according to the present invention may constitute any of a wide variety of already known or even as yet unidentified types of expression vector, such as viral, bacterial or plasmid expressing vector systems. Examples of suitable viral vectors include HSV, lentivirus, retroviral vectors and adeno-associated viral vectors. Preferred vectors are adenoviral vectors. Naturally, the expression vector adopted must be one which can transfect, e.g., infect, and result in protein expression in corneal tissue cells and particularly cells of the corneal epithelium, stroma and/or endothelium. Preferably, expression of the active agent, through infection by the expression vector, is within the endothelial cells and particularly preferably the level of infection of these cells with the selected expression vector is such that active ingredient expression is demonstrated in at least 5%, preferably at least 10%, more preferably at least 20%, particularly preferably at least 30% or at least 50% and most particularly preferably at least 70% in a sample of corneal endothelial cells. The expression vector selected will of course include all of the features required for expression of protein in a mammalian cell. For example, preferred expression vectors will contain a molecular chimera containing the coding sequence of active agent or agents selected, an appropriate polyadenylation signal for a mammalian gene (i.e. a polyadenylation signal which will function in a mammalian gene), and suitable enhancers and promoter sequences in the correct orientation.

In mammalian cells, normally two DNA sequences are required for the complete and efficient transcriptional regulation of genes that encode messenger RNAs in mammalian cells: promoters and enhancers. Promoters are located immediately upstream (5' from the start side of transcription. Promoter sequences are required for accurate and efficient initiation of transcription. Different gene-specific promoters reveal a common pattern or organization. A typical promoter includes an AT-rich region called a TATA box (which is located approximately 30 base pairs 5' to the transcription initiation start site) and one or more upstream promoter elements (UPE). The UPEs are a principle target for the interaction with sequence-specific nuclear transcription factors. The activity of promoter sequences is modulated by other sequences called enhancers. The enhancer sequence may be a great distance from the promoter in either upstream (5') or downstream (3') position. Hence, enhancers operate in an orientation- and position-independent manner. However, based on similar structural organization and function that may be interchanged the absolute distinction between promoters and enhancers is somewhat arbitrary. Enhancers increase the rate of transcription from the promoter sequence. The necessary machinery required for cellular expression of the active agent or agents must of course be located in the appropriate orientation with regard to the nucleotide sequence (preferably DNA) that encodes for the active agent or agents that has been inserted into the expression vector by the use of routine molecular biology techniques, such as, for example, as further explained in Ausubel et al. (1987) in: *Current Protocols in Molecular Biology*, Wyle Interscience (ISBN 047150338) the disclosure of which is incorporated by reference herein in its entirety. Also mentioned by way of reference in relation to preparation of expression vectors, the disclosure of which is included herein by reference is He et al., "A simplified system for generating recombinant adenovirus", *Proc. Nat. Acad. Sci.* (1998) 95: 2509-2514. The expression vector can appropriately include a suitable nuclear localisation signal and will be propagated in any permissive cell line. Permissive cell lines, mentioned by way of example only, include E1A and E1B trans-complementing 293 cells. Other cell lines will equally be useful for propagation of expression vectors according to the invention, as would clearly be understood by persons skilled in the art.

The exposure of corneal tissue to expression vectors according to the invention will be in a manner that will allow infection by the expression vector of the corneal tissue cells. The exposure of the corneal tissue to the expression vector can simply be by including the expression vector into the corneal tissue culture media. Other means of exposure such as via direct injection of the expression vectors into the corneal tissue or via high velocity bombardment may also be adopted, although care should be taken to avoid damage to the corneal tissue. To ensure adequate levels of infection of corneal cells with the expression vector it is necessary for an effective concentration for infection of the expression vector to be utilised. For example, concentrations of between about $1 \times 10^5$ and about $1 \times 10^{10}$ particle forming units (pfu) per cornea may be adopted. Preferably the effective concentration is between about $5 \times 10^5$ and $5 \times 10^8$ pfu/cornea, particularly preferably between about $2 \times 10^6$ and about $9 \times 10^7$ pfu per cornea. It is also important that the exposure of the corneal tissue to the expression vector is for a period sufficient to allow infection, such as for example between about 1 minute and about 48 hours, preferably between about 10 minutes and 24 hours, more preferably between about 30 minutes and about 6 hours and most preferably between about 1 hour and about 3 hours. This can, for example, be achieved by simply introducing the expression vector into the corneal tissue culture media and then changing the media to remove any remaining non-infected vector after the appropriate period, optionally with one or more washing stages.

The active agent which the corneal cells are modified to express can be one which is not expressed by normal corneal tissue or which, following modification is expressed at elevated levels relative to those of normal corneal tissue.

Also encompassed within the scope of the present invention are processes of improving corneal graft healing and/or prolonging graft survival involving the use of corneal tissue modified according to methods discussed above. When referring to "improving corneal graft healing" and "prolonging graft survival" these terms are intended to be relative to the rate and extent of healing and the duration of graft survival expected by conducting corneal allo-transplantation, without the administration to the patient of other graft healing or immunomodulatory agents.

Also included within the scope of the invention are the expression vectors prepared for use in methods according to the invention which allow for expression of active agents within corneal tissue cells, as well as the corneal tissue which comprises cells modified to express active agents.

The entire teachings of all patents, patent applications, books and references described or cited herein are hereby incorporated by reference in their entireties.

The present invention will now be described further, by way of example only, with reference to the following examples:

EXAMPLES

The inventors selected a model of orthotopic corneal transplantation in the outbred sheep, a relevant preclinical model in which unmodified corneal allografts undergo rejection at three weeks post-operatively in a manner that is very similar at a clinical level to human corneal graft rejection (9). Adenoviral vectors have already been shown to be capable of transferring reporter genes into corneal endothelium of various species (10-13) and the use of liposomal agents has also previously been explored (14, 15). Given that the mitotic potential of sheep corneal endothelium was unknown, the replicative capacity of this tissue was first examined, to allow an informed choice of the vector for gene therapy to be made. The immunomodulatory cytokine IL-10, which down-regulates cell-mediated immune responses under some circumstances (16, 17), was chosen as the candidate gene product for regulation of allograft rejection by ex vivo gene therapy.

Materials and Methods

Ovine corneal organ-culture. Fresh sheep eyes obtained within 3 hr of donor death from a local abattoir (Lobethal Abattoirs, Lobethal, SA, Australia) were decontaminated for 3 min in 10% w/v povidone-iodine (Faulding Pharmaceuticals, Salisbury, SA, Australia) and underwent two washes by immersion in sterile 0.9% w/v NaCl. A limbal incision was made with a scalpel blade and the cornea with a 2 mm scleral rim was removed with corneal scissors. Corneas were organ-cultured in 15 ml complete medium (HEPES-buffered RPMI medium (ICN, Costa Mesa, Calif., USA) supplemented with 10% v/v heat-inactivated (56° C., 30 min) fetal calf serum (FCS), 100 IU/ml penicillin, 100 µg/ml streptomycin, 2.5 µg/ml amphotericin B and 2 mM L-glutamine (all from Gibco BRL, Gaithersburg, Md., USA) at 32° C. in air for up to 28 days. Medium was changed twice weekly.

Evaluation of the mitotic potential of ovine corneal endothelium. A 4 mm long central cross-shaped defect was produced with a 27 gauge needle on endothelial monolayers of fresh ovine corneas. Corneas were then placed in sterile shallow wells, endothelium facing upward. 500 µl complete medium containing 25 µCi 6-$^3$H thymidine (TRA61; Amersham, Little Chalfont, Buckinghamshire, UK) was placed in the corneal cup for 5 hr at 32° C. The solution was then diluted to a total volume of 3 ml with complete medium containing no isotope and to 10 ml total after 24 hr. After 3 days, corneas were harvested, fixed in 3:1 absolute ethanol:glacial acetic acid at room temperature for 24 hr and transferred to 70% ethanol for a further 24 hr. Corneal endothelium was removed by blunt dissection through the stroma, mounted on gelatin-coated slides and air-dried for 2 hr. Flat-mounts were coated with LM-1 photographic autoradiography emulsion (Amersham, Little Chalfont, Buckinghamshire, UK), exposed at 4° C. for 4 weeks and processed according to the manufacturer's protocol. The flat-mounts were stained with Giemsa and mounted in Depex (BDH Chemicals, Kilsyth, VIC, Australia). As negative controls, corneas were injured and incubated in $^3$H thymidine-free medium, and uninjured corneas were incubated with and without $^3$H thymidine. Corneal epithelial flat-mounts prepared from corneas incubated as above with the epithelial surface in contact with tritiated thymidine-containing medium were used as a positive control.

Transfection of ovine corneal endothelium with adenoviral vectors. The replication deficient E1-, E3-deleted adenovirus type 5 vectors encoding $E.$ $coli$ lacZ under the transcriptional control of the CMV promoter (Ad-lacZ), or containing an empty plasmid (Ad-mock), or encoding full-length ovine IL-10 (Ad-IL-10) or P-40 subunit of IL-12 (Ad-P40-HL-12) (cDNA sequence provided by Dr S. Swinbum, Haematology Department, Flinders Medical Centre, South Australia) where prepared following the approach as described in Hu et al. as referenced above. cDNA sequences for these species are available on public databases. The Ad-lacZ construct contained a nuclear localization signal. Vectors were propagated in E1A, E1B trans-complementing 293 cells following standard protocols (18-20). In order to determine optimal viral concentration for infection of corneal endothelial cells, corneas were infected with concentrations of Ad-lacZ ranging from $6.6 \times 10^2$-$6.6 \times 10^8$ plaque forming units (pfu) per cornea in complete medium. Control corneas were uninfected or similarly infected with Ad-mock. Optimal infection time was determined by incubation of the corneas with $6.6 \times 10^6$ and $6.6 \times 10^7$ pfu Ad-lacZ per cornea for 0.5, 1, 1.5 and 2 hours; the vector was then diluted out and the corneas were re-incubated for a further 48 hr in 15 ml complete medium. To examine duration of reporter gene expression, corneas infected with $6.6 \times 10^7$ pfu per cornea for 2 hours at room temperature were organ-cultured for 2 days (n=14), 3 days (n=6), 6 days (n=6), 7 days (n=1), 10 days (n=5), 13 days (n=5), 14 days (n=1), 16 days (n=3), 21 days (n=4), and 28 days (n=3). After incubation, all corneas were processed for lacZ reporter gene expression.

Detection of lacZ reporter gene expression. Prior to processing, corneas were fixed in 2.5% formaldehyde and 0.25% glutaraldehyde in Dulbecco's A phosphate-buffered saline (PBS) for 15 min on ice followed by two 15 min washes in PBS on ice to inactivate the viral vector and inhibit endogenous β-galactosidase (21). Expression of $E.$ $coli$ β-galactosidase was detected using 2.5 ml/cornea of a solution of 1 mg/ml 5-bromo-4-chloro-3-indoxyl-β-D-galactoside (ICN, Costa Mesa, Calif., USA), N-dimethylfornamide (BDH Chemicals, Kilsyth, VIC, Australia), 2 mM $MgCl_2$, 5 mM $K_4Fe(CN)_6$, 5 mM $K_3Fe(CN)_6$ in PBS-2 (16 mM $Na_2HPO_4$, 4 mM $NaH_2PO_4.2H_2O$, 120 mM NaCl), pH 7.0 at 32° C. for 18 hr in the dark. After a 10 min wash with 20 ml water per cornea, a modified silver stain to stain endothelial cell boundaries was performed by application of 1% w/v $AgNO_3$ for 1 min and subsequent exposure to light (22). The endothelium was surgically removed using a 23 gauge needle and toothed forceps, and mounted in Kaiser's glycerol jelly (12.5% w/v gelatin, 87.5% v/v glycerin) on chrome-alum subbed slides. To detect E. coli β-galactosidase in 293 cells, cells were washed twice with PBS, fixed on ice with 0.25% glutaraldehyde in PBS for 5 min and washed twice with ice-cold PBS. Staining was then performed as described above.

Quantification of lacZ expression. To quantify the number of cells expressing the reporter gene, corneal endothelial flat-mounts were examined by light microscopy and photographed on 35 mm slide film at standard magnifications. The slides were projected at a standard distance and magnification. Total numbers of endothelial cells and lacZ positive cells were counted within frames of known dimension. For each cornea, three areas on each of two different slides taken of representative areas of the flat-mount were counted, and the mean and standard deviation (SD) calculated.

Detection of IL-10 mRNA in transfected ovine corneas. Fresh corneas prepared as described above were infected with $4.5 \times 10^6$ pfu Ad-mock or Ad-IL-10 for 2 hr or were incubated in medium without viral vector. They were then incubated in 3 ml complete medium at 32° C. in air for 24 hr, after which a further 2 ml of complete medium was added and organ-culture was continued. At various time points thereafter, a central 8 mm diameter full-thickness disc of cornea was trephined and snap-frozen in liquid nitrogen. Each disc was pulverised in a pre-chilled stainless steel mortar and pestle. Total RNA was extracted with Total RNA Extraction Reagent (Advanced Biotechnologies Ltd., Surrey, UK), treated with DNAse (GlassMax Microlsolation Kit, Life Technologies, Melbourne, VIC, Australia) and reverse-transcribed using a commercially-available first-strand cDNA synthesis kit (Amersham Pharmacia Biotech UK Limited, Buckinghamshire, England) according to the manufacturers' recommendations. To control for residual ovine genomic or viral DNA contamination, samples were subjected to the same reverse-transcription step after inactivation of the reverse transcriptase at 95° C. for 60 min. Dilutions of cDNA were amplified in 25 µl total volume by PCR. The reaction mixture for IL-10 and β-actin was 10 mM Tris-HCL (pH 8.3), 0.15M KCl (Perkin Elmer Roche Molecular Systems, Branchburg, N.J., USA), 0.2 mM of each dNTP (Amersham Pharmacia Biotech UK Limited, Buckinghamshire, England), 1.5 mM $MgCl_2$, 1 mM of each primer, 1 unit AmpliTaq-Gold (all from Perkin Elmer Roche Molecular Systems, Branchburg, N.J., USA) and 5 µl of sample. The reaction buffer for glyceraldehyde 3-phosphate dehydrogenase (GAPDH) contained 2 mM $MgCl_2$ but was otherwise identical. Primer sequences amplified a 307 base pair region for IL-10 (5'-GCAGCTGTACCCACTTCCCA-3', 5'-AGAAAACGATGACAGCG-3'), a 317 base pair region for β-actin (5'-ATCATGTTTGAGACCTTCAA-3',5'-CATCTCTTGCTCGAAGTCCA-3'), and a 527 base pair region for GAPDH (5'-ACCACCATGGAGAAGGCTGG-3', 5'-CTCAGTGTAGCCCAGGATGC-3'). After one cycle of 15 min at 94° C., 40 cycles of amplification were performed, each consisting of annealing at 55° C. for 30 sec, extension at 72° C. for 30 sec and 94° C. for 1 min, final extension at 55° C. for 30 sec, 72° C. for 20 sec and 35° C. for 10 sec. Amplified products were electrophoresed on 1.5% agarose w/v gels.

Orthotopic corneal transplantation in sheep. Adult female Merino-cross breed sheep were acclimatised in groups of at least two animals for at least one week in indoor pens and were fed water ad libitum and chaff supplemented with lucerne hay. Twelve mm diameter penetrating corneal transplantation was performed as previously described (9) in the right eye only. Post-operative care and inspection were as previously described and every graft was examined at the slit-lamp each day. Groups of sheep received unmodified corneal grafts, corneas infected with Ad-mock, or corneas that had been infected with Ad-IL-10 or Ad-P40-L-12 according to optmised procedures. The order in which sheep were grafted was random amongst all groups. Rejection was defined as reported previously (9). In several sheep with long-surviving corneal grafts, attempts were made to induce rejection by placement of 8-0 braided silk sutures into the graft under general anaesthetic, as an inflammatory stimulus. Approval for all experimentation was obtained from the institutional Animal Welfare Committee.

End-point histology of corneal allografts. Corneal tissue was fixed in buffered formalin, embedded in paraffin wax, cut at 8 µm and stained with haematoxylin and eosin.

Immunoperoxidase staining of corneal allografts. Hybridoma culture supematants containing mouse mAbs to sheep cell-surface determinants were obtained from the Department of Veterinary Science, University of Melbourne, Parkville, VIC, Australia and included: SBU 41.19, anti-MHC class I monomorphic epitope (23); SBU 28.1, anti-MHC class II monomorphic epitope (24); SBU 1-11-32, anti-CD45/leucocyte-common (unrestricted) antigen (25); SBU 44.38, anti-CD4 and SBU 38.65, anti-CD8 (26, 27); SBU 20.27, anti-CD1 (28); and SBU 72.87, anti-CD11a/LFA-1 (29). Culture supematants from the hybridomas P3X63Ag8 (IgGI isotype; European Collection of Animal Cell Cultures, Porton Down, Wiltshire, UK) and SAL5 (IgG2a isotype; gift of Dr L Ashman, IMVS, Adelaide, SA, Australia) were used as negative controls. Grafted eyes were harvested immediately post-mortem and the cornea excised, fixed, stained and scored as previously described (9).

Adenoviral antibody titres in fluids from sheep with corneal allografts. Immediately post-mortem, anterior chamber fluid was collected and snap-frozen at −80° C. Venous peripheral blood was also collected, the serun separated and similarly snap-frozen. Antibody titres to adenovirus were determined by a standard complement fixation test in the local reference laboratory using reagents from Biowhittaker Northfield Laboratories, Adelaide, SA, Australia.

Statistical analysis of data. Corneal graft survival data were analysed with the Mann-Whitney U-test, corrected for ties.

Results

Replicative capacity of ovine corneal endothelium. Ovine corneal endothelium was deliberately injured and the corneas organ-cultured in the presence of $^3H$ thymidine. The site of injury was still clearly visible at the light microscope on corneal endothelial flat-mounts harvested after 3 days in organ-culture. Uptake of $^3H$ thymidine into the nuclei of the occasional endothelial cell close to the site of the injury was observed (FIG. 1A) and very rare mitotic Figures were identified (FIG. 1B). Uptake of $^3H$ thymidine was limited to the close vicinity of the injury: no uptake occurred in the corneal periphery. Uninjured corneas (negative control) showed no uptake of $^3H$ thymidine and corneas incubated with the epithelial surface in contact with isotope-containing solution (positive control) showed substantial uptake (not shown). The data suggested that the replicative capacity of ovine corneal endothelium was very limited and that, for example, replication-deficient adenoviral virus (which remains episomal) would thus be a suitable vector for gene transfer to ovine endothelium.

Figure 2:
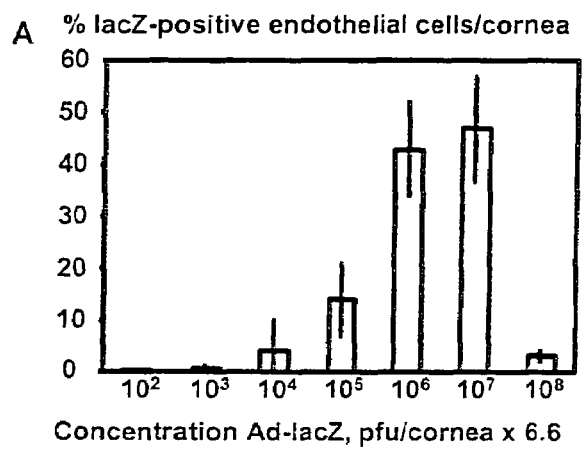
FIG. 2. Effect of viral concentration and incubation time with virus on transfection efficiency of the adenoviral vector Ad-lacZ for ovine corneal endothelium, and stability of expression of β-galactosidase in endothelial cells of organ-cultured ovine corneas. In each instance, reporter gene expression was quantified by counting β-galactosidase-positive cells in three representative areas per cornea.
Figure 2:
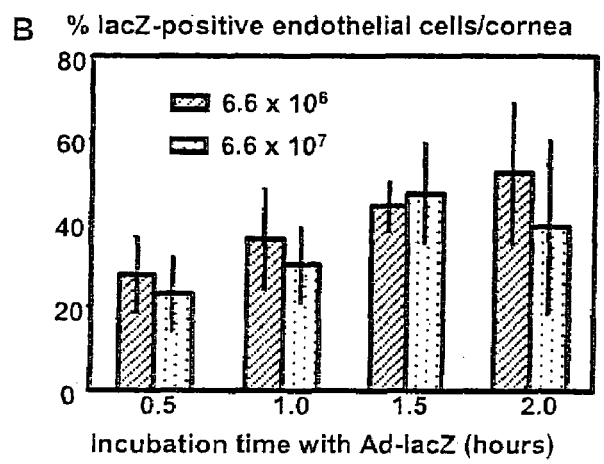
Figure 2:
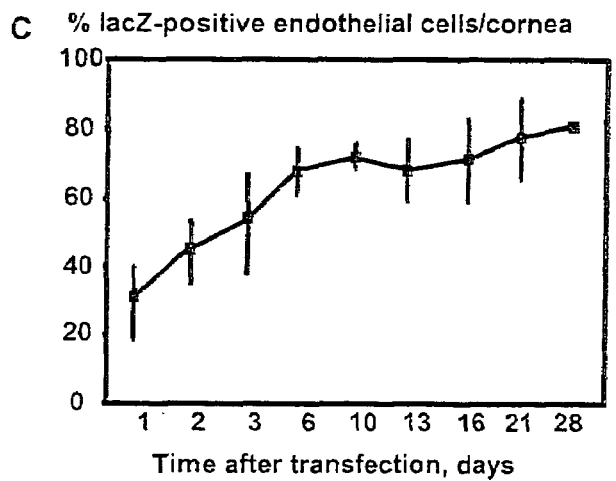

Adenoviral-mediated reporter gene transfer to ovine corneal endothelium. Ovine corneas were transfected in vitro with Ad-lacZ. At $6.6\times10^2$-$6.6\times10^4$ pfu/cornea, single β-galactosidase-positive cells were observed scattered over the endothelial monolayer. Increasing the virus concentration increased the number of β-galactosidase-positive cells to a maximum of approximately 50% (FIG. 2A), although a drop in expression was observed at $6.6\times10^8$ pfu/cornea. A concentration of $6.6\times10^{6-7}$ pfu/cornea was judged to yield optimal expression. None of the negative controls (no virus applied, Ad-mock applied) showed expression of β-galactosidase at any time. Reporter gene expression was observed only in corneal endothelium, not in stromal keratocytes. No visible toxic effects on the cornea were observed at any virus concentration. The influence of varying the time that the vector was in contact with corneal endothelium was investigated at $6.6\times10^6$ and $6.6\times10^7$ pfu/cornea (FIG. 2B): about 30% of cells were infected within the first hour, the number of positive cells increasing to about 50% at 2 hours. Duration of reporter gene expression was examined in a time-course experiment using $6.6\times10^7$ pfu/cornea and an infection time of 1.5 hr: 30% cells expressed β-galactosidase after 24 hr, rising to approximately 70% at day 6, and expression remained at this level for the 28-day observation period (FIG. 2C).

Figure 3:
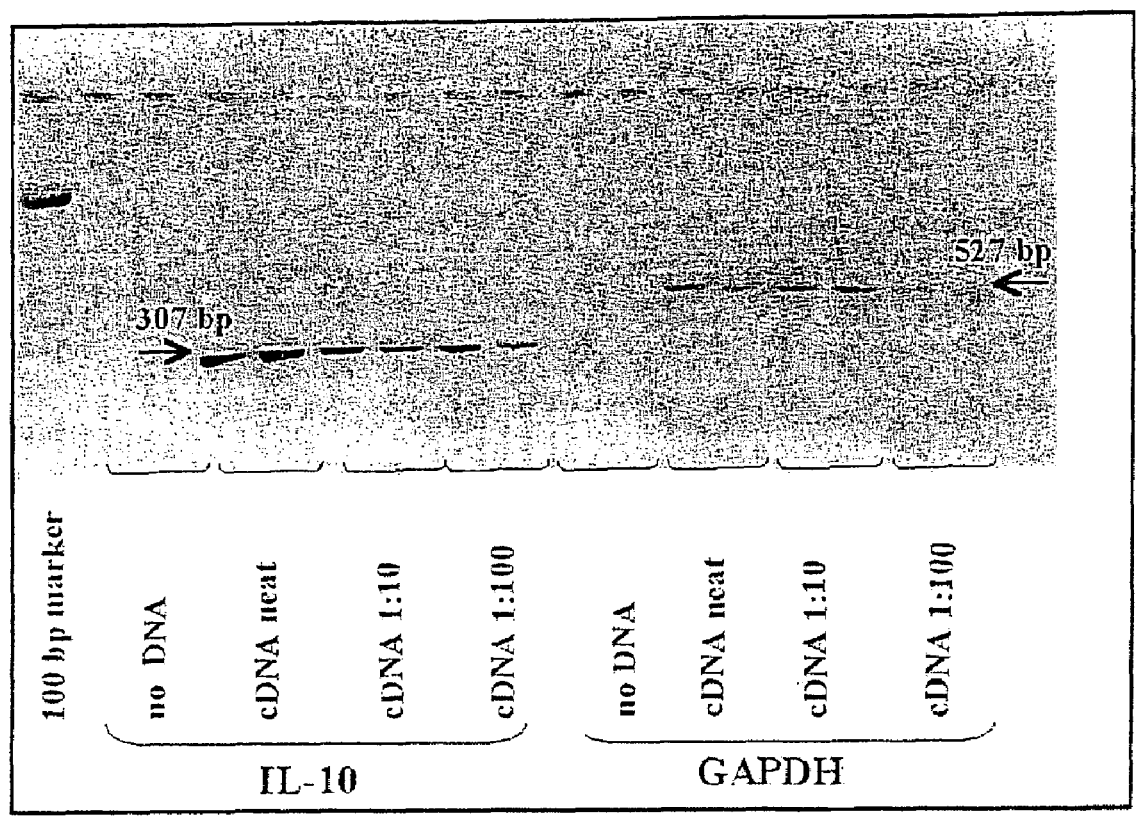
FIG. 3. Agarose 1.5% gel showing product for IL-10 and GAPDH in sheep corneas transfected with Ad-IL-10 under optimal conditions and organ-cultured for 21 days prior to RNA extraction and RT-PCR. Dilutions of cDNA at 1/1, 1/10 and 1/100 dilutions were run in duplicate lanes. Lanes marked no DNA represent controls in which water replaced cDNA.

Detection of IL-10 mRNA in IL-10 gene-modified organ-cultured ovine corneas. Ad-IL-10 was used to transfer the gene encoding ovine IL-10 into sheep corneal endothelium using conditions optimised for reporter gene expression, and the corneas were cultured in vitro for up to 21 days. Reverse transcription PCR was used to detect presence of mRNA for IL-10; β-actin and GAPDH served as housekeeping controls. No amplification of genomic or adenoviral IL-10 was observed in controls in which the reverse transcriptase had been inactivated after DNAse-I treatment of the isolated RNA preparations. Specific mRNA for ovine IL-10 was observed 24 hr after adenoviral infection and at various time points thereafter (Table 1), and could still be detected after corneas had been organ-cultured for 21 days (FIG. 3).

Figure 4:
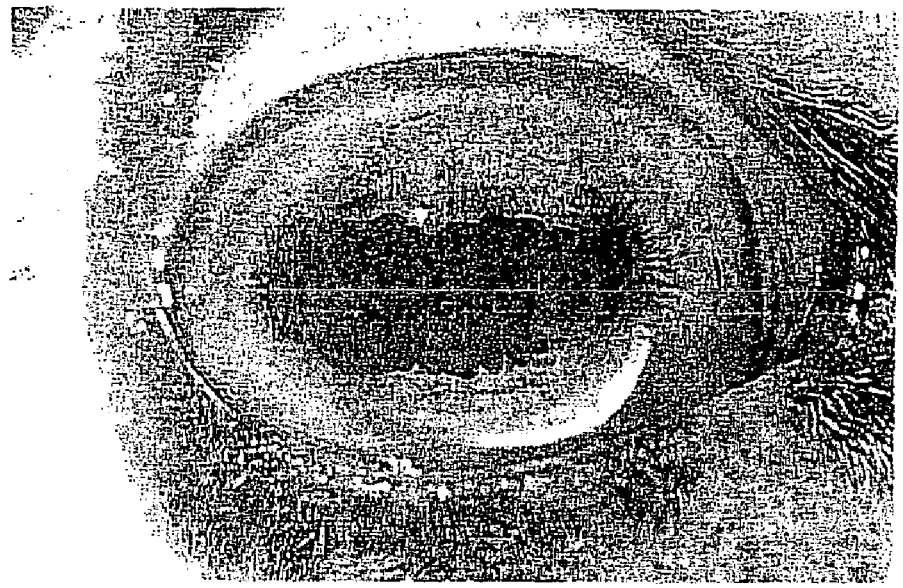
FIG. 4. Outcome of gene-modified penetrating corneal allografts in sheep.
Figure 4:
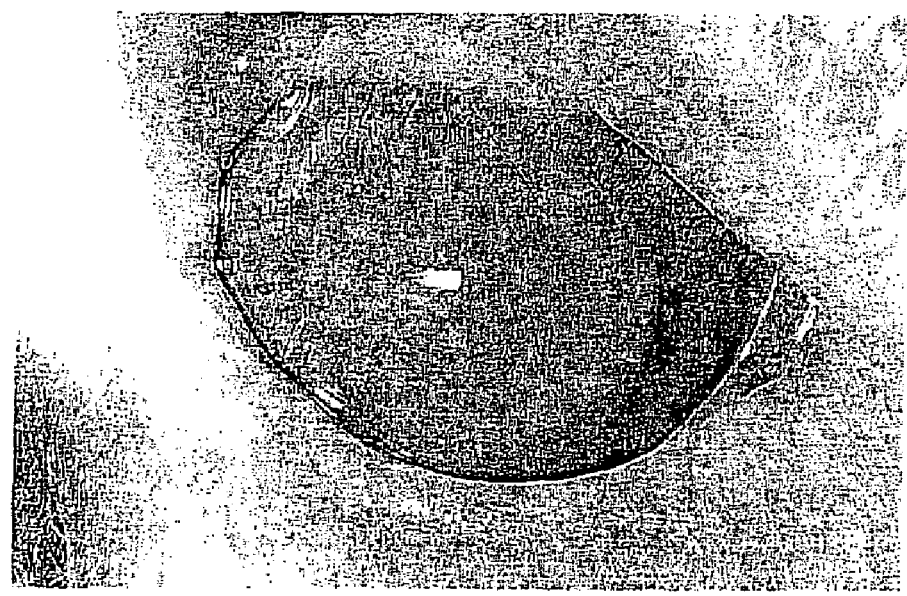

Orthotopic transplantation of gene-modified donor corneas in outbred sheep. The Ad-IL-10 and Ad-P40-IL-12 vectors were used to infect corneal endothelium of donor corneas immediately prior to orthotopic corneal transplantation in outbred sheep (FIG. 4). Controls included unmodified donor corneas and corneas infected with Ad-mock. Corneal graft survival data are shown in Table 2: corneal grafts modified by insertion of the gene encoding IL-10 into the donor endothelium survived significantly longer than unmodified controls ($p=0.019$) or the combined unmodified and mock virus-infected control groups ($p=0.011$). There was no difference in the time at which host vessels crossed the graft-host-junction amongst the groups ($p>0.05$). Longer survival was also demonstrated in corneas modified by c-section of the genes encoding the P40 subunit of L-12 (median 45 days). Post-operative inflammation was no more severe, and lasted for no longer, in the groups receiving adenovirus-treated corneas compared with the controls. End-point histology in sheep that showed clinical rejection of their grafts showed a similar picture in all instances: there was no difference amongst the experimental groups. Similarly, immunoperoxidase staining showed that rejecting gene-modified corneas contained a cellular infiltrate similar to that seen in rejecting unmodified or mock virus-infected grafts, with a substantial infiltrate of both CD4-positive and CD8-positive cells. No antibody to adenovirus was detectable in anterior chamber fluid or serum from 2 sheep at post-mortem.

Attempts were made to induce rejection in two sheep from the IL-10 group with gene-modified, long-surviving (>150 days) corneal grafts by placement of silk sutures into the graft at 196 and 303 days post-graft, respectively. In both cases, inflammation of the graft ensued and rejection occurred within two weeks, indicating that neither recipient was tolerant of the graft. Immunohistochemistry indicated that the infiltrate in these rejected grafts was similar to that seen in unmodified grafts.

Discussion $^3$H thymidine is incorporated into DNA by proliferating cells and can be visualised by autoradiography. This method has been used previously (30-33) to investigate the mitotic activity of corneal endothelium in many species. In the sheep cornea, uninjured endothelia incubated with $^3$H thymidine did not take up the isotope. Localized uptake into single endothelial cells was observed after deliberate injury, but proliferation was insufficient to cover the defect over three days. Our data suggest that ovine corneal endothelium has a very limited mitotic potential: some proliferation can be induced by a triggering event, but does not otherwise occur. For practical purposes, then, ovine corneal endothelium may be considered essentially amitotic. This resembles the situation in human and cat, where little mitosis occurs and defects are mainly covered by gradual sliding and enlargement of existing cells (30-33).

Replication-deficient adenoviruses, which remain episomal and do not integrate into the host genome, are suitable vectors for gene therapy of amitotic cells. A replication-defective adenovirus proved an efficient vector for gene transfer to 70-80% of ovine corneal endothelial cells. Optimal expression of the reporter gene in vitro was obtained with $6.6\times10^6$ pfu per cornea. Given that the sheep cornea contains approximately $8\times10^5$ endothelial cells, $6.6\times10^6$ pfu represents a multiplicity of infection of >10 virions per cell. Infection at higher concentrations of the vector was less efficient, but no obvious toxic effects were apparent at any viral concentration. The optimal concentration was similar to that found by other authors for infection of rabbit corneal endothelium with adenoviral vectors (13-15). Other authors have observed reporter gene expression in 7% of rabbit corneal endothelial cells using Lipofectamine (14), and in a relatively small proportion of bovine endothelial cells using dioleoyl phosphatidylethanolamine (34). More recently, George and his colleagues have demonstrated that activated polyamidoamine dendrimers, a novel class of non-viral agent, can successfully be used to transfer a gene into 6-10% of rabbit and human corneal endothelial cells (35). Adenovirus, however, appears significantly more efficient in achieving gene transfer than are non-viral agents.

Adenovirus binds to surface receptors and enters the cell by endocytosis via clathrin-coated vesicles, a fast process (36, 37). DNA replication in replicative adenoviruses starts approximately 8 hours after infection (38). In the sheep cornea, most adenoviral infection occurred within the first hour, but a delay of 5-6 days was observed before reporter gene expression was maximal. A time lag of 3-7 days for lacZ expression driven by either the CMV or RSV promoter has been observed after adenoviral transfer to human corneal endothelium (12, 14, 15). We observed lacZ expression in the sheep corneal endothelium to be stable for 4 weeks in vitro.

Investigators working in the rabbit have found expression of lacZ for 3-4 weeks in in vitro experiments (38), but for only 1-2 weeks after orthotopic corneal transplantation (10). The protein β-galactosidase has a half-life of 2 weeks in neurons (39) but shorter expression has been observed in other tissues such as respiratory epithelium (40), possibly due to gene silencing by promoter extinction (41). In the absence of a monoclonal antibody specific for ovine IL-10, expression of L-10 product in ovine corneal endothelial cells was assessed indirectly by detection of mRNA for IL-10 in transfected, organ-cultured corneas. We were able to detect IL-10 mRNA in ovine corneal endothelium for at least 3 weeks in vitro.

In the absence of immunosuppression, corneal graft rejection in the sheep occurs at approximately three weeks post-operatively (9). We therefore reasoned that expression of a transferred gene encoding an immunomodulatory cytokine for 3-4 weeks in vivo might be sufficient to modulate graft rejection. Inflammatory responses in the eye following reporter gene transfer have been reported previously (13), and similar findings have been observed in other immunoprivileged tissues such as brain (42). However, we considered it possible that expression of an immunomodulatory cytokine in a privileged site such as the eye might be sufficient to ameliorate any local immune responses to the viral vector, as well as to the allograft. Interestingly, Qin and colleagues have previously reported modulation of the immune response to both alloantigen and adenovirus antigens in a murine cardiac allograft model following adenoviral-mediated gene therapy with viral IL-10 (43).

Obvious toxicity that could be attributed to the use of the adenoviral vector was absent. The adenoviral construct used to deliver the target gene to donor corneal endothelium did not elicit a measurable antibody response in the sheep after corneal transplantation, and did not induce noticeable ocular inflammation over the time-course of the experiment. Host vessels extended from the limbus towards all corneal grafts at the same rate, irrespective of the experimental group. In most animals that received gene-modified donor corneas, neovascularization was not accompanied by corneal graft rejection and the corneal vessels in these sheep did not maintain patency.

In our experiments, gene transfer of IL-10 to the donor cornea immediately prior to transplantation prolonged corneal allograft survival to a significant extent in the cohort as a whole. In two cases, graft survival was prolonged indefinitely (>150 days). Allograft survival was also prolonged in the group where corneal tissue was modified with P-40 of IL-12. It is notable that these result were obtained without the use of any other immunosuppressive therapy at all and in particular, without use of topical glucocorticosteroid. However, some sheep with IL-10-modified donor corneas rejected their grafts within the same time-frame as did the control animals. In these animals, graft rejection was indistinguishable at either a macroscopic or microscopic level from that observed in the controls. In particular, the extent and composition of the leucocytic infiltrate was similar in all cases and there was no obvious difference in expression of MHC class I or II molecules within the graft. That tolerance was not induced in the long-survivors is evinced by the observation that these animals did reject their grafts after deliberate application of an inflammatory stimulus to the graft. We hypothesize that expression of IL-10 by corneal endothelium was sufficient to modulate or significantly delay rejection in the majority of animals, but that rejection overwhelmed the immunomodulation in a minority of recipients.

Both cellular (44-46) and viral IL-10 (43, 47-49) have been reported to prolong allograft survival and to modulate chronic rejection in a variety of small animal models, and IL-10 gene knock-out mice show decreased cardiac allograft survival and increased evidence of chronic rejection (50, 51). However, in at least one report, systemic administration of murine IL-10 was shown to exacerbate murine cardiac allograft rejection (52), and further, subconjunctival and systemic administration of various doses of murine IL-10 has been shown to be ineffective in prolonging corneal graft survival in the rat (53). The effect of IL-10 on allograft survival appears to be dependent upon both timing of administration (45) and upon dose (46). Mouse and human IL-10 may not be entirely homologous with respect to function: in particular, the former can be immunostimulatory for murine T cells (16), a property not shared by human IL1-10 or viral IL-10, although it has been suggested informally that endotoxin levels in various cytokine preparations may have affected some results. Ovine IL-10 has been shown to inhibit inflammatory cytokine production by sheep macrophages (54) and we believe it may have functional properties akin to human IL-10.

In summary, we report that delivery of genes encoding an immunomodulatory cytokines, mammalian IL-10 and P-40 subunit of L-12, into donor corneal endothelium prior to transplantation results in significant prolongation of corneal allograft survival in an outbred model in which the endothelium is essentially non-replicative, and in which rejection appears very similar to human corneal graft rejection at both clinical and histological levels.

The present invention has been described by way of example only and it should be recognised that modifications and/or alterations to the specific aspects of the invention which would be apparent to persons skilled in the art based on the disclosure herein, are also considered to fall within the spirit and scope of the invention.

TABLE 1

Detection of mRNAs for ovine IL-10 or housekeeping genes β-actin and GAPDH in ovine corneas after infection with adenoviral vectors[a]

| Time after infection | Primer identity | Corneas infected with:[a] | | |
|---|---|---|---|---|
| | | medium control | Ad-mock[b] | Ad-IL-10[c] |
| 2 hours | IL-10 | −[d] | − | (+)[d] |
| | β-actin/GAPDH | +[d] | + | + |
| 3 days | IL-10 | − | − | + |
| | β-actin/GAPDH | + | + | + |
| 7 days | IL-10 | − | − | + |
| | β-actin/GAPDH | + | + | + |
| 10 days | IL-10 | NT[e] | − | + |
| | β-actin/GAPDH | NT | + | + |
| 14 days | IL-10 | NT | − | + |
| | β-actin/GAPDH | NT | + | + |
| 21 days | IL-10 | NT | − | + |
| | β-actin/GAPDH | NT | + | + |

[a]For each primer at each time-point, 1-3 individual corneas were examined;
[b]Ad-mock, replication deficient E1, E3-deleted adenovirus type 5 containing an empty plasmid;
[c]Ad-IL-10, replication deficient E1, E3-deleted adenovirus type 5 encoding full-length ovine IL-10;
[d]− represents no signal detected by PCR, (+) represents a weak positive signal detectable only in an undiluted cDNA sample, + represents a strong positive signal;
[e]NT, not tested.

TABLE 2

Survival of control and gene-modified orthotopic corneal grafts in outbred sheep transplanted with unmodified donor corneas, or with corneas transfected before transplantation with Ad-mock, or with corneas transfected before transplantation with Ad-IL-10, Ad-P40-IL-12 or Ad-Il-4

| Donor cornea | n | Day vessels crossed into graft[a] | Day of rejection |
|---|---|---|---|
| Unmodified | 7 | 11, 10, 9, 8, 10, 9, 9 median = 9 | 18, 19, 19, 20, 20, 22, 32 median = 20 |
| Mock-transfected | 3 | 5, 7, 8 median = 7 | 19, 21, 29 median = 21 |
| IL-10-transfected | 9 | 5, 9, 9, 10, 10, 9, 11, 11, 9 median = 9 | 19, 20, 30, 33, 55, 66, 88, >196, >300[b] median = 55 |
| P-40 IL-12 transfected | 9 | — | 22, 23, 32, 36, 45, >50, 93, 93, >100 median = 45 |

[a]For each recipient sheep, the day post-graft at which corneal blood vessels crossed from the recipient corneal edge into the graft is shown, together with the day post-graft at which the graft was deemed to have undergone rejection. Individual recipients in columns 3 and 4 are listed in the same order; [b]p = 0.019 compared with unmodified controls, p = 0.011 compared with combined control groups (Mann-Whitney test, two-tailed).

REFERENCES

1. Williams K A, Muehlberg S M, Lewis R F, Coster D J on behalf of all contributors to the Australian Corneal Graft Registry (ACGR). How successful is corneal transplantation? A report from the Australian Corneal Graft Register. Eye 1995; 9:219.
2. Griffith T S, Ferguson T A. The role of FasL-induced apoptosis in immune privilege. Immunology Today 1997; 18: 240.
3. Williams K A, Coster D J. Clinical and experimental aspects of corneal transplantation. Transplantation Reviews 1993; 7: 44.
4. Pepose J S, Gardner K M, Nestor M S, Foos R Y, Pettit T H. Detection of HLA class I and II antigens in rejected human corneal allografts. Ophthalmology 1985; 92:1480.
5. Holland E J, Chan C-C, Wetzig R P, Palestine A G, Nussenblatt R B. Clinical and immunohistologic studies of corneal rejection in the rat penetrating keratoplasty model. Cornea 1991; 10: 374.
6. Whitcup S M, Nussenblatt R B, Price F W, Chan C-C. Expression of cell adhesion molecules in corneal graft rejection. Cornea 1993; 12: 475.
7. Sano Y, Osawa H, Sotozono C, Kinoshita S. Cytokine expression during orthotopic corneal allograft rejection in mice. Invest Ophthalmol Vis Sci 1998; 39:1953.
8. Tuft S J, Coster D J. The corneal endothelium. Eye 1990; 4:3 89.
9. Williams K A, Standfield S D, Mills R A, et al. A new model of orthotopic penetrating corneal transplantation in the sheep: graft survival, phenotypes of infiltrating cells and local cytokine production. Aust NZ J Ophthalmol 1999; 27: 127.
10. Larkin D F, Oral H B, Ring C J, Lemoine N R, George A J. Adenovirus-mediated gene delivery to the corneal endothelium. Transplantation 1996; 613: 363.
11. Borras T, Tamm E R, Zigler J S Jr. Ocular adenovirus gene transfer varies in efficiency and inflammatory response. Invest Ophthalmol Vis Sci 1996; 37: 1282.
12. Budenz D L, Bennett J, Alonso L, Maguire A. In vivo gene transfer into murine corneal endothelial and trabecular meshwork cells. Invest Ophthalmol Vis Sci 1995; 36:2211.
13. Oral H B, Larkin D F, Fehervari Z, et al. Ex vivo adenovirus-mediated gene transfer and immunomodulatory protein production in human cornea. Gene Therapy 1997; 4: 639.
14. Arancibia-Carcamo C V, Oral H B, Haskard D O, Larkin D F, George A J. Lipoadenofection-mediated gene delivery to the corneal endothelium: prospects for modulating graft rejection. Transplantation 1998; 65: 62.
15. Fehervari Z, Rayner S A, Oral H B, George A J, Larkin D F. Gene transfer to ex-vivo stored corneas. Cornea 1997; 16: 459.
16. De Waal Malefyt R, Yssel H, Roncarolo M-G, Spits H, de Vries J E. Interleukin-10. Current Opin Immunol 1992; 4: 314.
17. Moore K W, O Garra A, de Waal Malefyt R, Vieira P, Mosmann T R. Interleukin-10. Annu Rev. Immmunol 1993; 11:165.
18. Graham F L, Prevec L. Manipulation of adenovirus vectors. In: Murray E J, ed Methods in Molecular Biology Gene Transfer and Expression Protocols, Vol. 7. Clifton, N.J.: The Humana Press, 1991: 109.
19. Graham F, Smiley J, Russell W C, Nairn R. Characteristics of a human cell line transformed by DNA from human adenovirus type 5. J Gen Virol 1977; 36: 59.
20. Kanegae Y, Makimura M, Saito I. A simple and efficient method for purification of infectious recombinant adenovirus. Japn J Med Sci Biol 1994; 47: 157.
21. Lojda Z, Gossrau R, Schiebler T H. In: Enzymhistochemische Methoden. Berlin-Heidelberg: Springer Verlag, 1976: 128.
22. Sherrard E. The corneal endothelium in vivo: its response to mild trauma. Exp Eye Res 1976; 22: 347.
23. Gogolin-Ewens K J, Mackay C R, Mercer W R, Brandon M R. Sheep lymphocyte antigens (OLA). I Major histocompatibility complex class I molecules. Immunology 1985: 56: 717.
24. Puri N K, Mackay C R, Brandon M R. Sheep lymphocyte antigens (OLA). II Major histocompatibility complex class II molecules. Immunology 1985; 56: 725.
25. Maddox J F, Mackay C R, Brandon M R. The sheep analogue of leucocyte common antigen (LCA). Immunology 1985; 55: 347.
26. Mackay C R, Maddox J F, Brandon M R. Surface antigens, SBU-14 and SBU-T8, of sheep T lymphocyte subsets defined by monoclonal antibodies. Immunology 1985; 55:739.
27. Mackay C R, Maddox J F, Brandon M R. Three distinct subpopulations of sheep T lymphocytes. Eur J Immunol 1986: 16: 19.
28. Mackay C R, Maddox J F, Gogolin-Ewens K J, Brandon M R. Characterization of two sheep lymphocytic differentiation antigens, SBU-T1 and SBU-T6. Immunology 1085; 55: 729.
29. Grooby W L, Carter J K, Rao M M, et al. Use of an anti-LFA-1 antibody allograft rejection in sheep. Transplant. Proc 1992; 24: 2304.
30. Van Horn D L, Sendele D D, Seideman S, Buco P J. Regenerative capacity of the corneal endothelium in rabbit and cat. Invest Ophthamol Vis Sci 1977; 16: 597.
31. Simonsen A H, Sorensen K E, Sperling S. Thymidine incorporation by human endothelium during organ culture. Acta Ophthalmol 1981; 59: 110.
32. Tuft S J, Williams K A, Coster D J. Endothelial repair in the rat cornea. Invest Ophthalmol Vis Sci 1986; 27: 1199.
33. Treffers W F. 1982. Corneal endothelial wound healing. Nijmegen: Janssen Print, 1982.

34. Pleyer U, Druegg A, Bertelmann E, et al. Liposome-mediated gene transfer into corneal endothelial cells. Invest Ophthalmol Vis Sci 1997: 38: S402.
35. Hudde T, Rayner S A, Corner R M, et al. Activated polyamidoamine dendrimers, a non-viral vector for gene transfer to the corneal endothelium. Gene Therapy 1999; 6:939.
36. Philipson L, Lonberg-Holm K, Pettersson U. Virus-receptor interaction in an adenovirus system. J Virol 1968; 2: 1064.
37. Seth P, Fitzgerald D, H, Willingham M, Pastan I. Evidence that the penton base of adenovirus is involved in potentiation of toxicity of Pseudomonas exotoxin conjugated to epidermal growth factor. Mol Cell Biol 1984; 4: 1528.
38. Hoffman L M, Maguire A M, Bennett J. Cell-mediated immune response and stability of intraocular transgene expression after adenovirus-mediated delivery. Invest Ophthalmol Vis Sci 1997; 38: 2224.
39. Bloom D C, Maidment N T, Tan A, Dissette V B, Feldman L T, Stevens J G. Long term expression of a reporter gene from latent herpes simplex virus in the rat hippocampus. Brain Res Mol Brain Research 1995; 31: 48.
40. Goldman M J, Litzky L A, Engelhardt J F, Wilson J M. Transfer of the CFTR gene to the lung of nonhuman primates with E1-deleted, E2a-defective recombinant adenoviruses: a preclinical toxicology study. Hum Gene Therapy 1995; 6: 839.
41. Palmer T D, Rosman G J, Osborne W R, Miller A D. Genetically modified skin fibroblasts persist long after transplantation but gradually inactivate introduced genes. Proc Natl Acad Sci USA 1991; 88: 1330.
42. Byrnes A P, Rusby J E, Wood M J, Charlton H M. Adenovirus gene transfer causes inflammation in the brain. Neuroscience 1995; 66: 1015.
43. Qin L, Ding Y, Pahud D R, Robson N D, Shaked A, Bromberg J S. Adenovirus-mediated gene transfer of viral interleukin-10 inhibits the immune response to both alloantigen and adenoviral antigen. Hum Gene Ther 1997; 8: 1365.
44. Shinozaki K, Yahata H, Tanji H, Sakaguchi T, Ito H, Dohi K. Allograft transduction of IL-10 prolongs survival following orthotopic liver transplantation. Gene Therapy 1999; 6:816.
45. Boehler A, Chamberlain D, Xing Z, et al. Adenovirus-mediated interleukin-10 gene transfer inhibits post-transplant fibrous airway obliteration in an animal model of bronchiolitis obliterans. Hum Gene Therapy 1998; 9: 541.
46. Zou X M, Yagihashi A, Hirata K, et al. Downregulation of cytokine-induced neutrophil chemoattractant and prolongation of rat liver allograft survival by interleukin-10. Surg Today 1998; 28:184.
47. Qin L, Chavin K D, Ding Y, et al. Retrovirus-mediated transfer of viral IL-10 prolongs murine cardiac allograft survival. J Immunol 1996; 156: 2316.
48. DeBruyne L A, Li K, Chan S Y, Bishop D K, Bromberg J S. Lipid-mediated gene transfer of viral IL-10 prolongs vascularized cardiac allograft survival by inhibiting donor-specific cellular and humoral immune responses. Gene Therapy 1998; 5:1079.
49. Brauner R, Nonoyama M, Laks H, et al. Intracoronary adenovirus-mediated transfer of immunosuppressive cytokine genes prolongs allograft survival. J Thorac Cardiovasc Surg 1997; 114: 923.
50. Räisänen-Sokolowski A, Mottram P I, Glysing-Jensen T, Satoskar A, Russell M E. Heart transplants in interferon-γ, interleukin 4, and interleukin 10 knockout mice. Recipient environment alters graft rejection. J Clin Invest 1997; 100: 2449.
51. Räisänen-Sokolowski A, Glysing-Jensen T, Russell M E. Leukocyte-suppressing influences of interleukin (IL)-10 in cardiac allografts. Insights from IL-10 knockout mice. Am J Pathol 1998; 153: 1491.
52. Qian S, Li W, Li Y, et al. Systemic administration of cellular interleukin-10 can exacerbate cardiac allograft rejection in mice. Transplantation 1996; 62: 1709.
53. Torres P F, de Vos A F, Martins B, Kijlstra A. Interleukin 10 treatment does not prolong experimental corneal allograft survival. Ophthalmic Res 1999 31:2 97. Martin H M, Nash A D, Andrews A E. Cloning and characterisation of an ovine interleukin-10-encoding cDNA. Gene 1995; 159: 187.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of improving corneal graft healing and/or prolonging graft survival, wherein the method comprises exposing harvested corneal tissue to an effective concentration of an expression vector which comprises a nucleotide sequence encoding for a cytokine selected from IL-10 and the P-40 component of IL-12 for a period sufficient to allow transfection, and then transplanting the corneal tissue to an eye of a recipient such that cells of said corneal tissue will express the cytokine.

2. The method according to claim 1, wherein the nucleotide sequence consists of DNA.

3. The method according to claim 1, wherein the corneal tissue is harvested from a mammal.

4. The method according to claim 3, wherein the mammal is a human.

5. The method according to claim 1, wherein the corneal tissue cells modified are selected from the group consisting of epithelial cells, stroma cells, endothelial cells and combinations thereof.

6. The method according to claim 1, wherein the corneal cells modified are endothelial cells.

7. The method according to claim 6, wherein at least 5% of a sample of corneal endothelial cells are modified.

8. The method according to claim 6, wherein at least 10% of a sample of corneal endothelial cells are modified.

9. The method according to claim 6, wherein at least 20% of a sample of corneal endothelial cells are modified.

10. The method according to claim 6, wherein at least 30% of a sample of corneal endothelial cells are modified.

11. The method according to claim 6, wherein at least 50% of a sample of corneal endothelial cells are modified.

12. The method according to claim 6, wherein at least 70% of a sample of corneal endothelial cells are modified.

13. The method according to claim 1, wherein the effective concentration is between $1\times10^5$ to $1\times10^{10}$ particle forming units (PFU) per cornea.

14. The method according to claim 1, wherein the effective concentration is between $5\times10^5$ to $5\times10^8$ PFU per cornea.

15. The method according to claim 1, wherein the effective concentration is between $2\times10^6$ and $9\times10^7$ PFU per cornea.

16. The method according to claim 1, wherein exposing harvested corneal tissue to the expression vector is for a period between 1 minute and 48 hours.

17. The method according to claim 1, wherein exposing harvested corneal tissue to the expression vector is for a period between 10 minutes and 24 hours.

18. The method according to claim 1, wherein exposing harvested corneal tissue to the expression vector is for a period between 30 minutes and 6 hours.

19. The method according to claim 1, wherein the period sufficient to allow infection is between 1 hour and 3 hours.

20. The method according to claim 1, wherein the expression vector is selected from the group consisting of a viral, a bacterial and a plasmid vector.

21. The method according to claim 1, wherein the expression vector is an adeno associated viral vector or an adenoviral vector.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: primers

<400> SEQUENCE: 1
gcagctgtac ccacttccca                                            20

<210> SEQ ID NO 2
<211> LENGTH: 17
<212> TYPE: DNA
<213> ORGANISM: primers

<400> SEQUENCE: 2
agaaaacgat gacagcg                                               17
```

```
<210> SEQ ID NO 3
<211> LENGTH: 20
<212> TYPE: DNA
<213> ORGANISM: primers

<400> SEQUENCE: 3
atcatgtttg agaccttcaa                                           20

<210> SEQ ID NO 4
<211> LENGTH: 20
<212> TYPE: DNA
<213> ORGANISM: primers

<400> SEQUENCE: 4
catctcttgc tcgaagtcca                                           20

<210> SEQ ID NO 5
<211> LENGTH: 20
<212> TYPE: DNA
<213> ORGANISM: primers

<400> SEQUENCE: 5
accaccatgg agaaggctgg                                           20

<210> SEQ ID NO 6
<211> LENGTH: 20
<212> TYPE: DNA
<213> ORGANISM: primers

<400> SEQUENCE: 6
ctcagtgtag cccaggatgc                                           20
```